US012779200B2

(12) United States Patent
Reynolds

(10) Patent No.: US 12,779,200 B2
(45) Date of Patent: Nov. 3, 2026

(54) PERCUTANEOUS CIRCULATORY SUPPORT DEVICE WITH EXPANDABLE ELEMENT

(71) Applicant: Boston Scientific Scimed Inc., Maple Grove, MN (US)

(72) Inventor: Brian Reynolds, Ramsey, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 697 days.

(21) Appl. No.: 18/118,556

(22) Filed: Mar. 7, 2023

(65) Prior Publication Data

US 2023/0285738 A1 Sep. 14, 2023

Related U.S. Application Data

(60) Provisional application No. 63/317,727, filed on Mar. 8, 2022.

(51) Int. Cl.

*A61M 60/13* (2021.01)
*A61M 25/00* (2006.01)
*A61M 60/174* (2021.01)
*A61M 60/216* (2021.01)

(52) U.S. Cl.

CPC .......... *A61M 60/13* (2021.01); *A61M 60/174* (2021.01); *A61M 60/216* (2021.01); *A61M 25/0074* (2013.01)

(58) Field of Classification Search

CPC .. A61M 60/13; A61M 60/174; A61M 60/216; A61M 25/0074

See application file for complete search history.

(56) References Cited

U.S. PATENT DOCUMENTS

| | | | | |
|---|---|---|---|---|
| 4,944,722 | A | | 7/1990 | Carriker et al. |
| 5,295,958 | A | | 3/1994 | Shturman |
| 5,370,618 | A | * | 12/1994 | Leonhardt ......... A61M 25/1034 604/103 |
| 5,527,159 | A | | 6/1996 | Bozeman, Jr. et al. |
| 5,692,882 | A | | 12/1997 | Bozeman, Jr. et al. |
| 5,911,685 | A | | 6/1999 | Siess et al. |

(Continued)

FOREIGN PATENT DOCUMENTS

| | | |
|---|---|---|
| EP | 847767 B1 | 2/2005 |
| EP | 2301598 B1 | 7/2017 |

(Continued)

OTHER PUBLICATIONS

US 9,067,007 B2, 06/2015, Tanner et al. (withdrawn)

(Continued)

*Primary Examiner* — Lindsey G Wehrheim

(74) *Attorney, Agent, or Firm* — Seager, Tufte & Wickhem LLP

(57) ABSTRACT

A percutaneous circulatory support device includes a housing, an impeller disposed within the housing and being rotatable relative to the housing, a cannula coupled to the housing, the cannula extending between a proximal portion and a distal portion of the cannula positioned opposite the proximal end, an expandable element arranged near the distal portion of the cannula, the expandable element capable of inflation and deflation, and wherein the expandable element is configured for providing an atraumatic portion at the distal portion of the cannula.

19 Claims, 7 Drawing Sheets

(56) References Cited

U.S. PATENT DOCUMENTS

| | | | |
|---|---|---|---|
| 5,947,892 | A | 9/1999 | Benkowski et al. |
| 6,135,729 | A | 10/2000 | Aber |
| 6,139,487 | A | 10/2000 | Siess |
| 6,176,822 | B1 | 1/2001 | Nix et al. |
| 6,176,848 | B1 | 1/2001 | Rau et al. |
| 7,731,675 | B2 | 6/2010 | Aboul-Hosn et al. |
| 7,841,976 | B2 | 11/2010 | McBride et al. |
| 7,927,068 | B2 | 4/2011 | McBride et al. |
| 7,972,122 | B2 | 7/2011 | Larose et al. |
| 8,376,707 | B2 | 2/2013 | McBride et al. |
| 8,591,393 | B2 | 11/2013 | Walters et al. |
| 8,597,170 | B2 | 12/2013 | Walters et al. |
| 8,641,752 | B1 | 2/2014 | Holm et al. |
| 8,684,904 | B2 | 4/2014 | Campbell et al. |
| 8,721,517 | B2 | 5/2014 | Zeng et al. |
| 8,992,163 | B2 | 3/2015 | McBride et al. |
| 9,072,825 | B2 | 7/2015 | Pfeffer et al. |
| 9,138,518 | B2 | 9/2015 | Yuen et al. |
| 9,162,017 | B2 | 10/2015 | Evans et al. |
| 9,308,302 | B2 | 4/2016 | Zeng |
| 9,308,304 | B2 | 4/2016 | Peters et al. |
| 9,327,067 | B2 | 5/2016 | Zeng et al. |
| 9,364,592 | B2 | 6/2016 | McBride et al. |
| 9,364,593 | B2 | 6/2016 | McBride et al. |
| 9,381,288 | B2 | 7/2016 | Schenck et al. |
| 9,421,311 | B2 | 8/2016 | Tanner et al. |
| 9,446,179 | B2 | 9/2016 | Keenan et al. |
| 9,675,740 | B2 | 6/2017 | Zeng et al. |
| 9,717,833 | B2 | 8/2017 | McBride et al. |
| 9,770,543 | B2 | 9/2017 | Tanner et al. |
| 9,872,947 | B2 | 1/2018 | Keenan et al. |
| 9,895,476 | B2 | 2/2018 | Larose et al. |
| 9,907,890 | B2 | 3/2018 | Muller |
| 9,956,332 | B2 | 5/2018 | Larose et al. |
| 9,962,475 | B2 | 5/2018 | Yuen et al. |
| 9,964,115 | B2 | 5/2018 | Scheckel |
| 10,029,037 | B2 | 7/2018 | Muller et al. |
| 10,039,872 | B2 | 8/2018 | Zeng et al. |
| 10,071,192 | B2 | 9/2018 | Zeng |
| 10,086,121 | B2 | 10/2018 | Fitzgerald et al. |
| 10,105,475 | B2 | 10/2018 | Muller |
| 10,107,299 | B2 | 10/2018 | Scheckel |
| 10,117,980 | B2 | 11/2018 | Keenan et al. |
| 10,149,932 | B2 | 12/2018 | McBride et al. |
| 10,215,187 | B2 | 2/2019 | McBride et al. |
| 10,232,099 | B2 | 3/2019 | Peters et al. |
| 10,251,985 | B2 | 4/2019 | Larose et al. |
| 10,251,986 | B2 | 4/2019 | Larose et al. |
| 10,478,539 | B2 | 11/2019 | Pfeffer et al. |
| 10,478,540 | B2 | 11/2019 | Scheckel et al. |
| 10,525,178 | B2 | 1/2020 | Zeng |
| 10,576,192 | B2 | 3/2020 | Muller et al. |
| 10,576,193 | B2 | 3/2020 | Tanner et al. |
| 10,709,829 | B2 | 7/2020 | Muller |
| 10,709,830 | B2 | 7/2020 | Tanner et al. |
| 10,765,789 | B2 | 9/2020 | Zeng et al. |
| 10,780,208 | B2 | 9/2020 | Siess et al. |
| 10,786,610 | B2 | 9/2020 | Zeng |
| 10,799,624 | B2 | 10/2020 | Pfeffer et al. |
| 10,842,921 | B2 | 11/2020 | Siess et al. |
| 10,864,308 | B2 | 12/2020 | Muller et al. |
| 10,864,309 | B2 | 12/2020 | McBride et al. |
| 10,874,783 | B2 | 12/2020 | Pfeffer et al. |
| 10,894,115 | B2 | 1/2021 | Pfeffer et al. |
| 10,918,774 | B2 | 2/2021 | Stanfield et al. |
| 10,960,116 | B2 | 3/2021 | Yuen et al. |
| 10,980,927 | B2 | 4/2021 | Pfeffer et al. |
| 11,020,582 | B2 | 6/2021 | Cambronne et al. |
| 11,058,865 | B2 | 7/2021 | Fitzgerald et al. |
| 11,110,264 | B2 | 9/2021 | Cambronne et al. |
| 11,123,539 | B2 | 9/2021 | Pfeffer et al. |
| 11,129,978 | B2 | 9/2021 | Pfeffer et al. |
| 11,167,124 | B2 | 11/2021 | Pfeffer et al. |
| 11,227,986 | B2 | 1/2022 | Male et al. |
| 11,235,138 | B2 | 2/2022 | Gross-Hardt et al. |
| 11,253,693 | B2 | 2/2022 | Pfeffer et al. |
| 11,260,213 | B2 | 3/2022 | Zeng et al. |
| 11,273,301 | B2 | 3/2022 | Pfeffer et al. |
| 11,311,712 | B2 | 4/2022 | Zeng et al. |
| 11,338,214 | B2 | 5/2022 | White et al. |
| 11,357,967 | B2 | 6/2022 | Zeng et al. |
| 11,400,276 | B2 | 8/2022 | Chopra et al. |
| 11,497,896 | B2 | 11/2022 | Tanner et al. |
| 11,517,736 | B2 | 12/2022 | Earles et al. |
| 11,517,737 | B2 | 12/2022 | Struthers et al. |
| 11,524,153 | B2 | 12/2022 | Alexander et al. |
| 11,583,659 | B2 | 2/2023 | Pfeffer et al. |
| 11,628,294 | B2 | 4/2023 | Chopra et al. |
| 11,666,747 | B2 | 6/2023 | Tuval et al. |
| 11,708,833 | B2 | 7/2023 | McBride et al. |
| 11,754,075 | B2 | 9/2023 | Schuelke et al. |
| 11,786,700 | B2 | 10/2023 | Pfeffer et al. |
| 11,813,445 | B2 | 11/2023 | Alexander et al. |
| 11,839,754 | B2 | 12/2023 | Tuval et al. |
| 2008/0114339 | A1 | 5/2008 | McBride et al. |
| 2008/0132747 | A1 | 6/2008 | Shifflette |
| 2008/0132748 | A1 | 6/2008 | Shifflette |
| 2008/0262337 | A1 | 10/2008 | Falwell et al. |
| 2009/0060743 | A1 | 3/2009 | McBride et al. |
| 2012/0041254 | A1 | 2/2012 | Scheckel |
| 2013/0303831 | A1 | 11/2013 | Evans |
| 2014/0107399 | A1 | 4/2014 | Spence |
| 2014/0200395 | A1 | 7/2014 | Shafi et al. |
| 2016/0096006 | A1 | 4/2016 | Cully et al. |
| 2016/0136343 | A1 | 5/2016 | Anagnostopoulos |
| 2017/0296725 | A1 | 10/2017 | Peters et al. |
| 2018/0126130 | A1* | 5/2018 | Nitzan ................. A61B 5/4878 |
| 2018/0303990 | A1 | 10/2018 | Siess et al. |
| 2018/0311423 | A1 | 11/2018 | Zeng et al. |
| 2019/0321530 | A1 | 10/2019 | Cambronne et al. |
| 2019/0344001 | A1 | 11/2019 | Salahieh et al. |
| 2020/0155743 | A1 | 5/2020 | Siess et al. |
| 2020/0237981 | A1* | 7/2020 | Tuval .................... F04D 29/545 |
| 2020/0237982 | A1 | 7/2020 | Tuval et al. |
| 2020/0323670 | A1 | 10/2020 | Honeyfield et al. |
| 2021/0015982 | A1 | 1/2021 | Kerkhoffs et al. |
| 2021/0038785 | A1 | 2/2021 | Siess et al. |
| 2021/0106810 | A1 | 4/2021 | Pfeffer et al. |
| 2022/0134082 | A1 | 5/2022 | Pfeffer et al. |
| 2023/0051191 | A1 | 2/2023 | Struthers et al. |
| 2023/0149690 | A1 | 5/2023 | Liu et al. |

FOREIGN PATENT DOCUMENTS

| | | | |
|---|---|---|---|
| EP | 3352808 | B1 | 9/2023 |
| WO | 2013025470 | A2 | 2/2013 |
| WO | 2013025470 | A3 | 2/2013 |
| WO | 2021119478 | A1 | 6/2021 |
| WO | 20230915563 | A1 | 5/2023 |

OTHER PUBLICATIONS

International Search Report and Written Opinion for International Application No. PCT/US2023/014727, dated Feb. 14, 2021. (13 pages).

* cited by examiner

PERCUTANEOUS CIRCULATORY SUPPORT DEVICE WITH EXPANDABLE ELEMENT

CROSS-REFERENCE TO RELATED APPLICATIONS

This application claims priority to U.S. Provisional Application No. 63/317,727, filed Mar. 8, 2022, which is herein incorporated by reference in its entirety.

TECHNICAL FIELD

The present disclosure relates to percutaneous circulatory support devices. More specifically, the present disclosure relates to percutaneous circulatory support devices including an expandable element.

BACKGROUND

Percutaneous circulatory support devices such as blood pumps can provide transient support for up to approximately several weeks in patients with compromised heart function or cardiac output. Several issues may complicate delivery and operation of blood pumps within the heart, including the blood pump potentially causing trauma to the vasculature or cardiac tissue and the oscillation and/or migration of the blood pump resulting in decreased performance of the blood pump.

SUMMARY

In an Example 1, a percutaneous circulatory support device includes a housing, an impeller disposed within the housing and being rotatable relative to the housing, a cannula coupled to the housing, the cannula extending between a proximal portion and a distal portion of the cannula positioned opposite the proximal end, an expandable element arranged near the distal portion of the cannula, the expandable element capable of inflation and deflation, and wherein the expandable element is configured for providing an atraumatic portion at the distal portion of the cannula.

In an Example 2, the device of Example 1 includes wherein the expandable element is a balloon.

In an Example 3, the device of Example 1 or Example 2 includes wherein the expandable element includes a lumen for receiving at least a portion of the cannula.

In an Example 4, the device of any one of Examples 1-3 includes wherein the expandable element includes an initial diameter and an inflated diameter, the inflated diameter being greater than the initial diameter.

In an Example 5, the device of Example 4 includes wherein the cannula comprises an outer diameter that is less than the inflated diameter of the expandable element.

In an Example 6, the device of any one of Examples 1-5 includes wherein the expandable element has a length that is less than a total length of the cannula.

In an Example 7, a percutaneous circulatory support device includes a housing, an impeller disposed within the housing and being rotatable relative to the housing to cause blood to flow through the housing, a cannula coupled to the housing, the cannula having a body extending between a proximal portion and a distal portion of the cannula positioned opposite the proximal portion and configured such that the blood may flow through the cannula, an expandable element arranged around the body of the cannula, the expandable element capable of inflation and deflation and wherein the expandable element is configured for providing an atraumatic tip of the cannula.

In an Example 8, the device of Example 7 further includes wherein the expandable element is positioned near the distal portion of the cannula.

In an Example 9, the device of Example 7 includes wherein the expandable element is positioned distal to a plurality of blood inlets of the cannula and distally of a distalmost end of the cannula.

In an Example 10, the device of any one of Examples 7-9 includes wherein the expandable element has an initial diameter and an inflated diameter, the expanded diameter being greater than the initial diameter.

In an Example 11, the device of any one of Examples 7-10 includes wherein the expandable element has a circular cross section and defines a lumen extending through the expandable element.

In an Example 12, a method for positioning a blood pump within a subject, the blood pump including a cannula having a body extending between a proximal portion and a distal tip portion of the cannula, and the cannula having an expandable element positioned around the cannula body at a position that is distal to the proximal portion and proximal to the distal tip portion, includes advancing the blood pump through the vasculature of the subject, inflating the expandable element from an initial diameter to an inflated diameter, and crossing the aortic valve of the subject with the blood pump such that the cannula is positioned at least partially in the left ventricle of the subject.

In an Example 13, the method of Example 12 includes wherein after inflating the expandable element, the expandable element comprises a circular cross-sectional shape.

In an Example 14, the method of Example 12 or Example 13 includes wherein an outer diameter of the cannula is less than the inflated diameter of the expandable element.

In an Example 15, the method of any one of Examples 12-14 includes wherein the expandable element is configured for providing an atraumatic tip.

In an Example 16, a percutaneous circulatory support device includes a housing having an outlet, an impeller disposed within the housing and being rotatable relative to the housing to cause blood to flow through the housing and out of the outlet, a cannula coupled to the housing, the cannula extending between a proximal portion and a distal portion of the cannula positioned opposite the proximal end, an expandable element arranged near the distal portion of the cannula, the expandable element capable of inflation and deflation, and wherein the expandable element is configured for providing an atraumatic portion at the distal portion of the cannula.

In an Example 17, the device of Example 16 includes wherein the expandable element is a balloon.

In an Example 18, the device of Example 16 includes wherein the expandable element includes a lumen for receiving at least a portion of the cannula.

In an Example 19, the device of Example 16 includes wherein the expandable element is composed of a polymer.

In an Example 20, the device of Example 16 includes wherein the expandable element comprises an initial diameter and an inflated diameter, the inflated diameter being greater than the initial diameter.

In an Example 21, the device of Example 20 includes wherein the cannula comprises an outer diameter that is less than the inflated diameter of the expandable element.

In an Example 22, the device of Example 16 includes wherein the expandable element has a length that is less than a total length of the cannula.

In an Example 23, the device of Example 16 includes wherein the expandable element has a cross-sectional shape that is generally circular.

In an Example 24, the device of Example 16 includes wherein the expandable element has a cross-sectional shape that is irregular in shape.

In an Example 25, a percutaneous circulatory support device includes a housing, an impeller disposed within the housing and being rotatable relative to the housing to cause blood to flow through the housing, a cannula coupled to the housing, the cannula having a body extending between a proximal portion and a distal portion of the cannula positioned opposite the proximal portion and configured such that the blood may flow through the cannula, an expandable element arranged around the body of the cannula, the expandable element capable of inflation and deflation, and wherein the expandable element is configured for providing an atraumatic tip of the cannula.

In an Example 26, the device of Example 25 further includes wherein the expandable element is positioned near the distal portion of the cannula.

In an Example 27, the device of Example 25 includes wherein the expandable element is positioned distal to a plurality of blood inlets of the cannula and distally of a distalmost end of the cannula.

In an Example 28, the device of Example 25 includes wherein the expandable element has an initial diameter and an inflated diameter, the expanded diameter being greater than the initial diameter.

In an Example 29, the device of Example 2 includes wherein the expandable element has a circular cross section and defines a lumen extending through the expandable element.

In an Example 30, a method for positioning a blood pump within a subject, the blood pump including a cannula having a body extending between a proximal portion and a distal tip portion of the cannula, and the cannula having an expandable element positioned around the cannula body at a position that is distal to the proximal portion and proximal to the distal tip portion, includes advancing the blood pump through the vasculature of the subject, inflating the expandable element from an initial diameter to an inflated diameter, and crossing the aortic valve of the subject with the blood pump such that the cannula is positioned at least partially in the left ventricle of the subject.

In an Example 31, the method of Example 30 includes wherein after inflating the expandable element, the expandable element comprises a circular cross-sectional shape.

In an Example 32, the method of Example 30 includes wherein an outer diameter of the cannula is less than the inflated diameter of the expandable element.

In an Example 33, the method of Example 30 includes wherein the expandable element is configured for providing an atraumatic tip.

In an Example 34, the method of Example 30 includes wherein the expandable element is a balloon.

In an Example 35, the method of Example 30 includes wherein the expandable element includes a lumen for receiving the body of the cannula.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION

Figure 1:
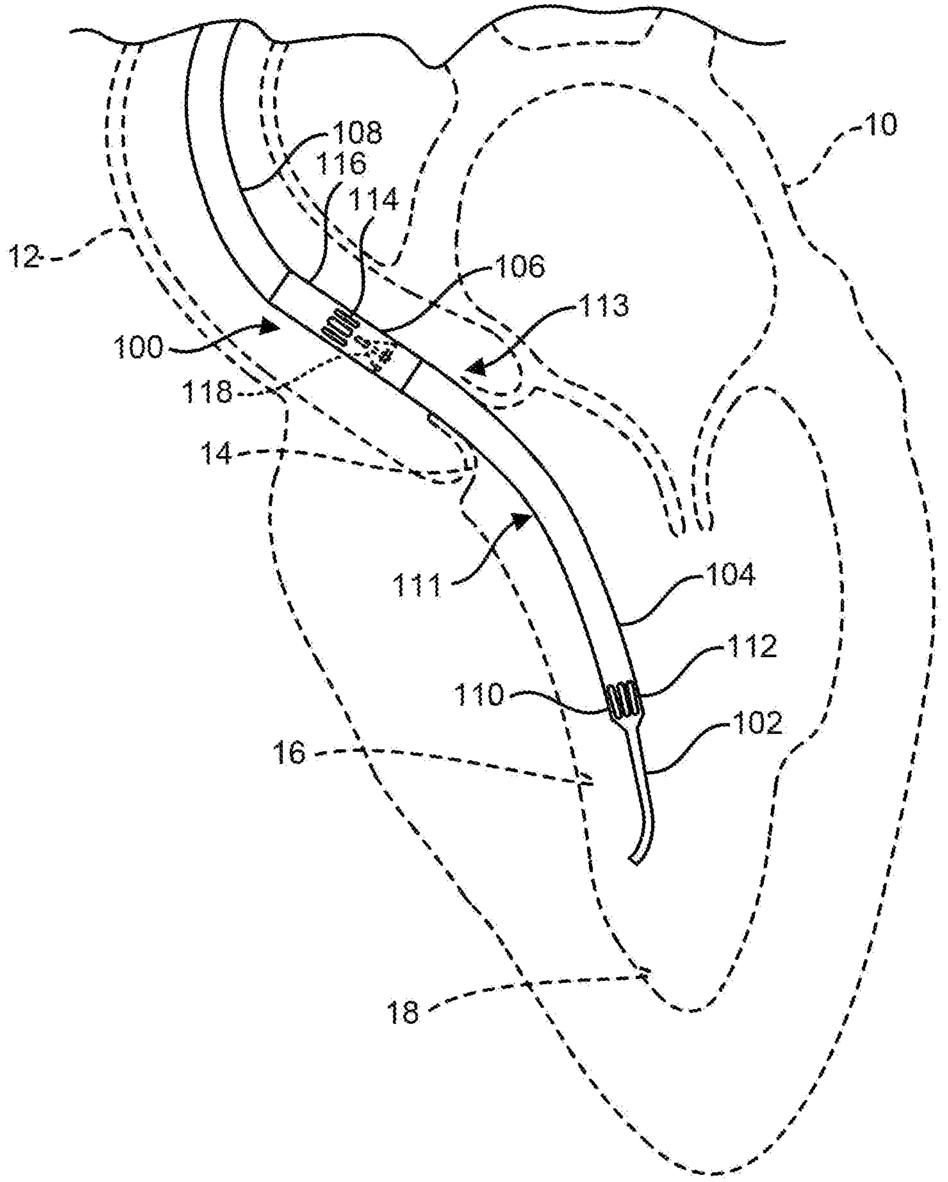
FIG. 1 illustrates a percutaneous circulatory support device after delivery into a patient's heart, in accordance with embodiments of the present disclosure.

FIG. 1 depicts a portion of an illustrative percutaneous mechanical circulatory support device 100 (also referred to herein, interchangeably, as a "blood pump"), and its relative position in a human heart 10, in accordance with embodiments of the subject matter disclosed herein. The blood pump 100 may be delivered percutaneously, for example, by passing the blood pump 100 through the vasculature, through the aorta 12, and then positioning the blood pump 100 within the heart 10 with respect to the aortic valve 14 and the left ventricle 16, as shown in FIG. 1. In some embodiments and as described in further detail below, the blood pump 100 may provide enhanced trackability and may be delivered without using an ancillary guidewire (not shown—that is, a guidewire separate from the blood pump 100). Alternatively, the blood pump 100 may be delivered using an ancillary guidewire.

With continued reference to FIG. 1, the blood pump 100 generally includes a distal tip portion 102, a cannula 104, an impeller portion 106, and a catheter 108. The cannula 104 may have a flexible construction to facilitate delivery of the blood pump 100. The cannula 104 includes one or more blood inlets 110 located on a distal portion 112 thereof, and one or more blood outlets 114 are located on a housing 116 of the impeller portion 106. A connector 124 may be positioned between the blood inlets 110 and the distal tip portion 102. The cannula 104 comprises a body 111 extending between the distal portion 112 and a proximal portion 113 of the cannula 104. More specifically, the distal portion 112 is positioned directly proximal to the inlets 110. The housing 116 carries an impeller 118, and the impeller 118 rotates relative to the housing 116 to cause blood to flow into the inlets 110, through the housing 116, and out of the outlets 114. During operation and as shown in FIG. 1, the blood pump 100 is positioned within the heart 10 such that the inlets 110 are positioned in the left ventricle 16 and the outlets 114 are positioned in the aorta 12. As a result, rotation of the impeller 118 relative to the housing 116 causes blood to flow from the left ventricle 16, through the cannula 104 and the impeller portion 106, and into the aorta 12. In some cases, during operation the blood pump 100 may be positioned such that the distal tip portion 102 is located in close proximity of, or in contact with, the wall of the left ventricle 16, for example, in the location of the apex 18 of the left ventricle 16.

Figure 2A:
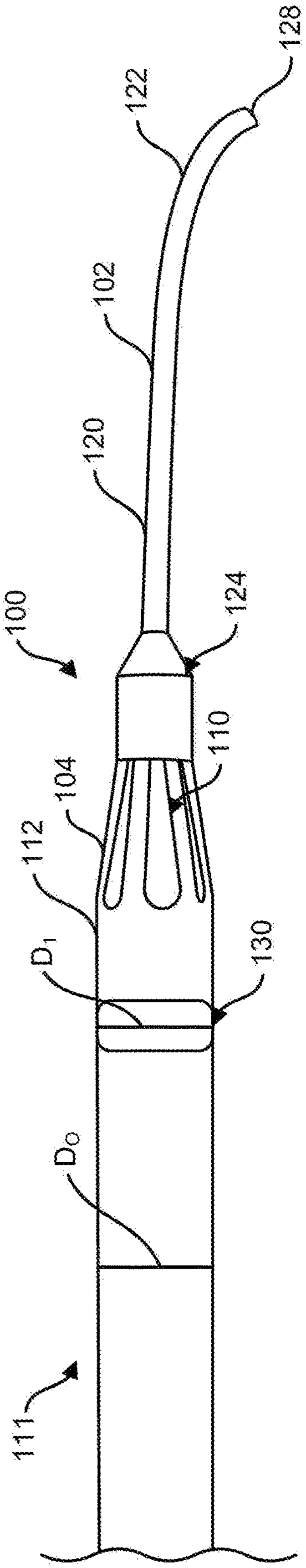
FIG. 2A illustrates a side view of a cannula of a percutaneous circulatory support device in a first configuration, in accordance with embodiments of the present disclosure.

FIG. 2A depicts a side view of a portion of the blood pump 100, specifically the distal portion 112 of the cannula 104, the connector 124 and the distal tip portion 102. The distal tip portion 102 includes a proximal section 120 adjacent to the cannula 104 and a distal section 122 adjacent to the proximal section 120 and opposite the cannula. In some embodiments and as illustrated, the proximal section 120 has a generally straight shape and the distal section 122 has a generally curved shape. In other embodiments, the proximal section 120 and/or the distal section 122 have different shapes. Additionally, the connector 124 may have a plurality of different shapes and sizes for connecting the distal portion 112 and the distal tip portion 102 of the cannula 104. The body 111 of the cannula 104 may be composed of a plurality of wires forming a structural body portion. In embodiments, the cannula 104 may also comprise a surface coating that is disposed onto the structural body portion of the cannula 104.

Further, as illustrated, the distal portion 112 of the cannula 104 includes an expandable element 130. Specifically, in the embodiment shown in FIG. 2A, the expandable element 130 is positioned within the distal portion 112 of the cannula 104 but proximal to the distal tip portion 102. However, in various embodiments, the distal tip portion 102 of the cannula 104 may be eliminated. Even further, the blood inlets 110 and the connector 124 may be eliminated as well and the end of the cannula 104 may have an open end. As such, in these embodiments, blood may flow into open end of the cannula 104 and through the body 111 of the cannula 104.

Figure 2B:
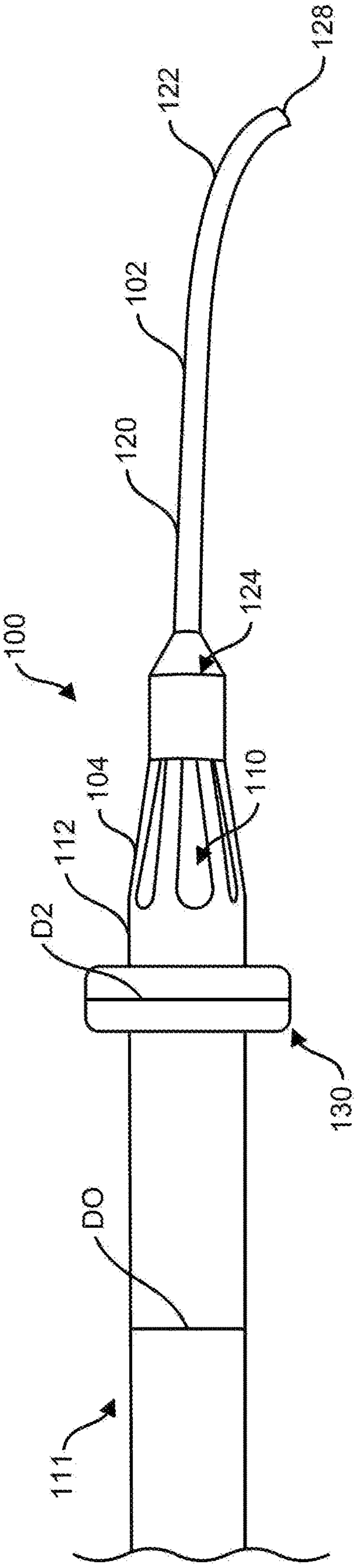
FIG. 2B illustrates a side view of a cannula of a percutaneous circulatory support device in a second configuration, in accordance with embodiments of the present disclosure.

The expandable element 130 is configured such that the expandable element 130 can be inflated and/or deflated. In some embodiments, the expandable element 130 may be a balloon, and for example, may be composed of a polymer. In other embodiments, the expandable element 130 may be composed of various other suitable materials that allow for the expandable element 130 to inflate and deflate. FIG. 2A illustrates the expandable element 130 in a deflated configuration, wherein the expandable element 130 has a first, initial diameter D1. The initial diameter D1 may be approximately equal to an outer diameter Do of the cannula 104. FIG. 2B illustrates the cannula 104 and the expandable element 130 after inflation of the expandable element 130 by the physician or operator. More specifically, the expandable element 130 includes a second, inflated diameter D2. The inflated diameter D2 may have a value that is greater than the value of the initial diameter D1, and as such is greater than the outer diameter Do of the cannula. The ability to inflate the expandable element 130 prior to, during and/or after placement of the blood pump 100, and more specifically of the cannula 104, provides enhanced trackability and steering of the cannula 104 to the desired position.

As mentioned above, in various embodiments, the distal tip portion 102 of the cannula 104, blood inlets 110, and/or connector 124 may be removed from the end of the cannula 104. In these embodiments, the cannula 104 may have an open end such that blood may flow into open end of the cannula 104 and through the body 111 of the cannula 104. As such, in these embodiments the configuration of the expandable element 130 allows for the distal portion 112 of cannula 104 to act as an atraumatic portion, e.g., an atraumatic tip of the blood pump. The expandable element 130 is generally smooth and lacks sharp protrusions, and consequently, if the expandable element 130 comes into contact with the vasculature or cardiac tissue of the subject, there is a reduced chance of damage to the vasculature or cardiac tissue, as compared to the edges, wall or other surface features of the outer surface of the cannula 104 or other structures of the blood pump 100 coming into contact with such tissues. The expandable element 130 may additionally be composed of a biocompatible material that contributes to the atraumatic characterization of the expandable element 130.

Figure 2C:
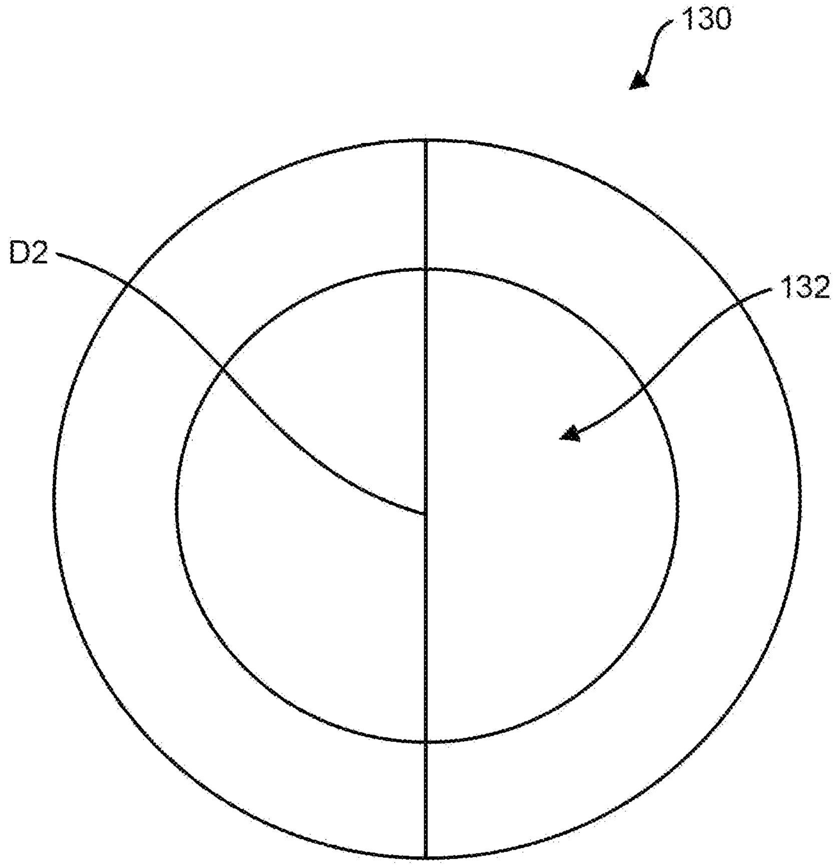
FIG. 2C illustrates a cross-sectional view of an expandable element for use with the cannula of FIG. 2A, in accordance with embodiments of the present disclosure.

FIG. 2C illustrates a cross section of the expandable element 130 after inflation, as is illustrated in FIG. 2B. Specifically, the expandable element 130 comprises a generally circular cross-sectional shape with a lumen 132 extending through the expandable element 130. While illustrated as having a generally circular cross-sectional shape, the expandable element 130 may comprise various other shapes. For example, the cross-sectional shape may be generally oval or rectangular in shape. In other embodiments, the cross-sectional shape may be an irregular shape. Additionally, while the lumen 132 is illustrated as having a generally circular cross-sectional shape, the shape may be varied. For example, the cross-sectional shape of the lumen 132 may be a rectangle, oval or an irregular shape. The above-described configuration of the expandable element 130 is not meant to be limiting, and various other configurations may be incorporated.

Figure 3:
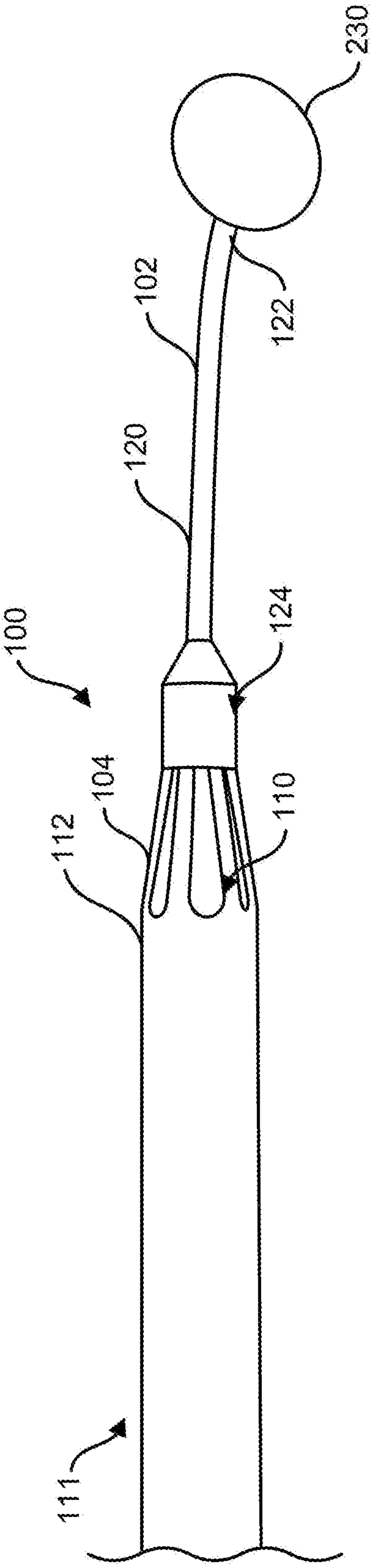
FIG. 3 illustrates a side view of a cannula of a percutaneous circulatory support device, in accordance with embodiments of the present disclosure.

For example, FIG. 3 illustrates an additional configuration of the blood pump 100 with an expandable element 230 positioned distally of the blood outlets 114 and entirely on the distal tip portion 102 of the cannula 104. More specifically, the expandable element 230 is positioned at the distalmost portion of the distal tip portion 102, however the expandable element 230 may be positioned at any point of the distal tip portion 102. In some embodiments, similar to the expandable element 130 as described with reference to FIGS. 2A-2C, the expandable element 230 may comprise a lumen (not shown) extending through the expandable element 230 and configured for receiving at least the distal section 122 of the distal tip portion 102. In this way, the expandable element 230 may be inflated and configured to form an atraumatic tip at the distal section 122 of the cannula 104. More specifically, as the cannula 104 is guided through the vasculature of the subject, the expandable element 230 may engage with the tissue of the vasculature without damaging the tissue. As described with reference to the expandable element 130 of FIGS. 2A-2C, the atraumatic characterization of the expandable element 230 ensures that while the cannula 104 is positioned or navigated through the vasculature, damage to the vasculature of the subject is minimized.

Additionally, as illustrated in FIG. 3, the expandable element 230 may be generally spherical in shape. However, various other shapes of the expandable element 230 may be incorporated. For example, the expandable element 230 may have an oval shape, a cylindrical shape, a rectangular shape and/or an irregular shape. Additionally, the expandable element 230 may have varying initial and inflated diameters, similar to the expandable element 230 shown in FIG. 2A.

The operator may have the ability to inflate the expandable element 230 to a desired inflation diameter based on the desired positioning and navigation of the cannula 104. For example, the expandable element 230 may be inflated to the inflated diameter D2 as described with reference to FIG. 2B. Further, the expandable element 230 may be composed of a polymer, similar to the expandable element 130 as described with reference to FIGS. 2A-2C. The positioning of the expandable element 230 may also vary, as will be described further with reference to FIGS. 4A-4B.

Figure 4A:
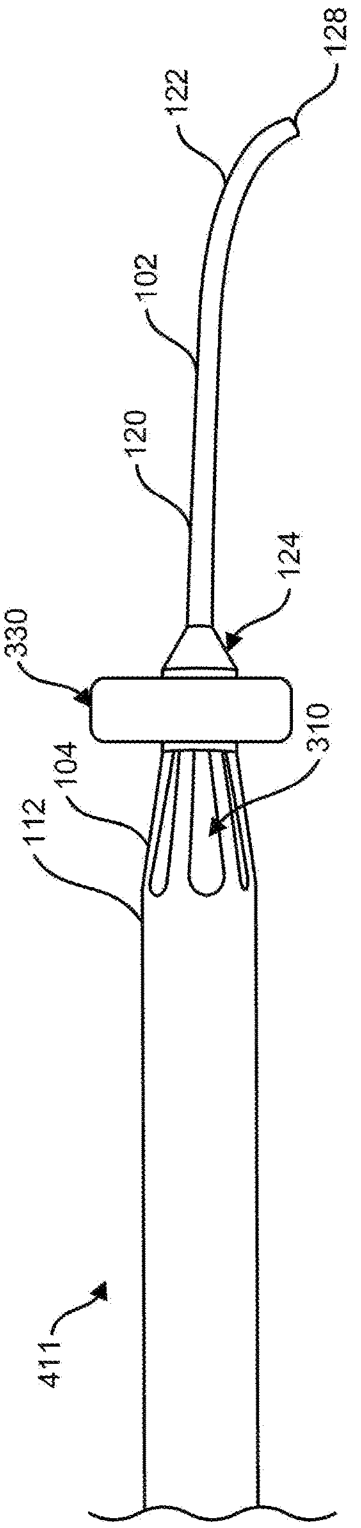
FIG. 4A illustrates a side view of a cannula of a percutaneous circulatory support device, in accordance with embodiments of the present disclosure.
Figure 4B:
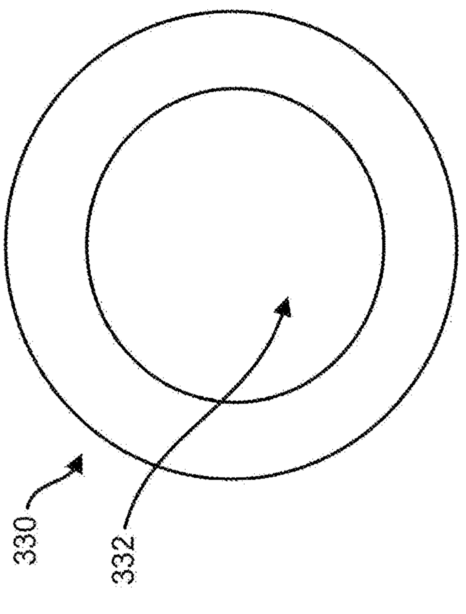
FIG. 4B illustrates a cross-sectional view of an expandable element for use with the cannula of FIG. 4A, in accordance with embodiments of the present disclosure.

FIG. 4A illustrates an additional embodiment of the cannula 104 and an alternative embodiment of an expandable element 330. More specifically, the expandable element 330 may be positioned distal to the distal portion 112 of the cannula 104 and distal to the inlets 110, but still proximal to the distal tip portion 102. For example, the expandable element 330 may be positioned on the connector 124. In these embodiments, the expandable element 330 may comprise a circular configuration with a lumen extending therethrough. More specifically, FIG. 4B illustrates a cross-sectional view of the expandable element 330, the expandable element comprising a lumen 332 extending through the expandable element 330. In this way, blood is able to flow through the lumen 332 within the expandable element 330 and through the inlets 110. As illustrated, the cross-sectional shape of both the expandable element 330 and the lumen 332 is generally circular. However, in various embodiments, the cross-sectional shape of the expandable element 330 may be varied, for example generally rectangular, oval or otherwise irregular in shape. Similarly, the lumen 332 may be rectangular, oval, or otherwise irregular in shape. Additionally, the size of the expandable element 330 and the size of the lumen 332 may be varied for the desired use as well.

Figure 5A:
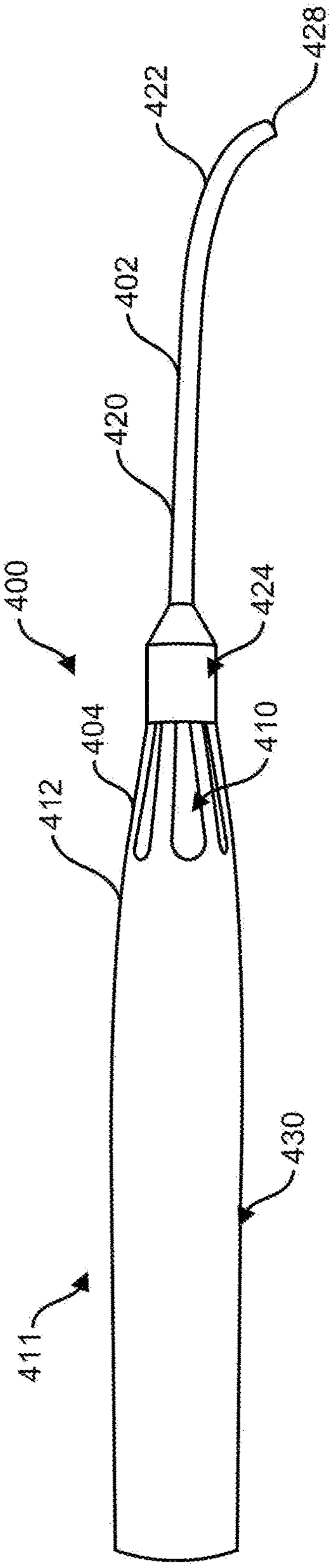
FIG. 5A illustrates a side view of a cannula of a percutaneous circulatory support device, in accordance with embodiments of the present disclosure.
Figure 5B:
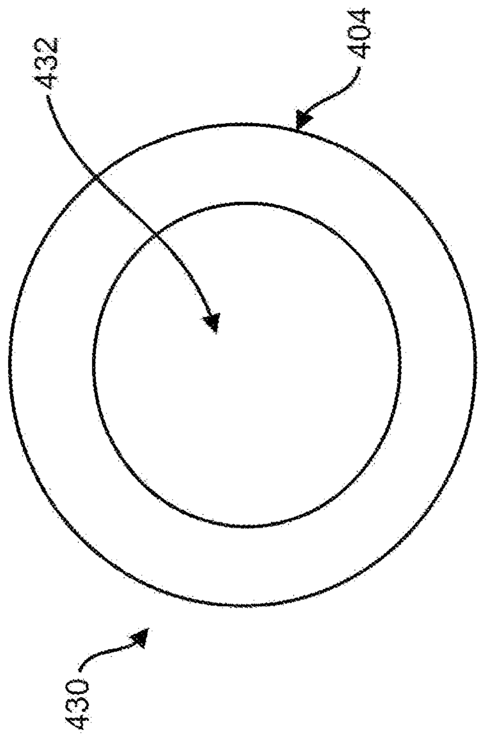
FIG. 5B illustrates a cross-sectional view of the cannula of FIG. 5A, in accordance with embodiments of the present disclosure.

FIG. 5A illustrates an additional embodiment of a portion of a blood pump 400, and more specifically, an inflatable cannula 404. The cannula 404 of FIG. 5A may be similar to that of the cannula 104 described above with reference to FIGS. 1-4, with the exception that a body 411 of the cannula 404 is inflatable. More specifically, the body 411 of the cannula 404 may be composed of an expandable element 430 that may be inflated and/or deflated during use. In other words, the expandable element 430 may be a balloon and as such, the body 411 of the cannula 404 may be configured as an inflatable balloon. While the cannula 104 is illustrated as having the blood inlets 410 and the distal tip portion 402, in various embodiments, the cannula 404 does not compose these elements. In other words, the blood inlets 410, the connector 424, and the distal tip portion 402 are eliminated in such various embodiments. In this way, the expandable element 430 defines the body 411 of the cannula 404 and the distal portion 412 acts a blood inlet to the cannula 404. FIG. 5B illustrates a cross-sectional view of the expandable element 430, and as such the body 411 of the cannula 404. As illustrated, the expandable element 430 may have a generally circular cross section such that the expandable element 430 defines a lumen 432 extending through the expandable element 430. The lumen 432 may then act as a lumen of the cannula 404 itself, configured to receive the blood that flows through the blood pump 400. The expandable element 430 may comprise various other cross-sectional shapes. For example, the expandable element 430 may have an oval, rectangular or otherwise irregular in shape. Similarly, the shape of the lumen 432 may vary as well. For example, the lumen 432 may have an oval or rectangular cross section.

The above-described configuration of the cannula 404 allows for an atraumatic configuration of the cannula 404. In other words, while maneuvering the blood pump 400, if the cannula 404 comes into contact with the vasculature of the subject, the potential for damage to the vasculature is reduced as compared to a cannula composed of a stent like structure or otherwise protruding surfaces. As the entire cannula 404 may be composed of the expandable element 430, contact with the vasculature at any point along the cannula 404 may not impart any damage to the vasculature of the subject. Additionally, the ability to inflate and/or deflate the expandable element 430 may provide additional physician control of the blood pump 400 and may allow for patient-specific customization of the blood pump 400. For example, the expandable element 430 can be inflated and deflated by the physician to aid in the correct positioning of the cannula 404 within the vasculature, as will be described further herein.

Figure 6:
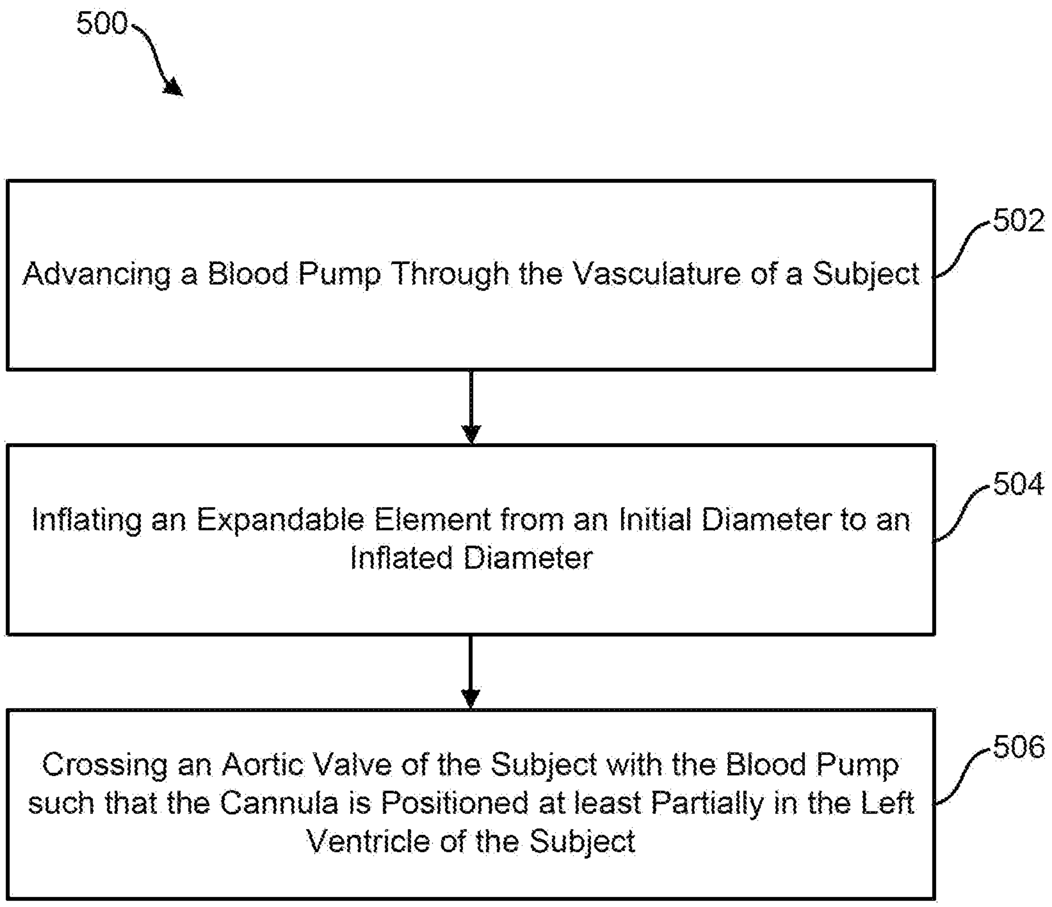
FIG. 6 illustrates a flow chart of a method for positioning a percutaneous circulatory support device, in accordance with embodiments of the present disclosure.

FIG. 6 illustrates a flow chart of a method 500 for positioning the blood pump within a subject. At block 502, the method 500 includes advancing the blood pump into the vasculature of the subject. At block 504, the method 500 further includes inflating the expandable element 130 from the initial diameter D1 to the inflated diameter D2. In embodiments, this step may be accomplished by the physician through manipulating a delivery device of the blood pump 100. More specifically, the catheter 108 (FIG. 1) may include mechanisms and/or actuators that allow for inflation and deflation of the expandable element 130 and are positioned to be available to the physician throughout the procedure.

At block 506, the method 500 further includes crossing an aortic valve of the subject with the blood pump 100 such that the cannula 104 is positioned at least partially in the left ventricle of the subject. In various embodiments, the method 500 may further include inflating and/or deflating the expandable element 130 if desired to reposition the blood pump 100. While the above-described method is described with reference to the expandable element 130 and the cannula 104 of FIGS. 2A-2C, the method 500 may be applied with the expandable elements 230, 330, 430 and the cannula 404 described with reference to FIGS. 3-5B.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above-described features.

The invention claimed is:

1. A percutaneous circulatory support device, comprising:

a housing comprising a blood outlet;

an impeller disposed within the housing and being rotatable relative to the housing to cause blood to flow through the housing and out of the outlet;

a cannula coupled to the housing, the cannula extending between a proximal portion and a distal portion of the cannula positioned opposite the proximal end;

a blood inlet positioned proximate the distal portion, wherein the impeller is configured to convey blood flow through the cannula from the blood inlet to the blood outlet;

an expandable element arranged near the distal portion of the cannula, the expandable element positioned proximal to the blood inlet, the expandable element capable of inflation and deflation; and wherein the expandable element is configured for providing an atraumatic portion along the cannula.

2. The percutaneous circulatory support device of claim 1, wherein the expandable element is a balloon.

3. The percutaneous circulatory support device of claim 1, wherein the expandable element comprises a lumen for receiving at least a portion of the cannula.

4. The percutaneous circulatory support device of claim 1, wherein the expandable element is composed of a polymer.

5. The percutaneous circulatory support device of claim 1, wherein the expandable element comprises an initial diameter and an inflated diameter, the inflated diameter being greater than the initial diameter.

6. The percutaneous circulatory support device of claim 5, wherein the cannula comprises an outer diameter that is less than the inflated diameter of the expandable element.

7. The percutaneous circulatory support device of claim 1, wherein the expandable element has a length that is less than a total length of the cannula.

8. The percutaneous circulatory support device of claim 1, wherein the expandable element has a cross-sectional shape that is generally circular.

9. The percutaneous circulatory support device of claim 1, wherein the expandable element has a cross-sectional shape that is irregular in shape.

10. A percutaneous circulatory support device, comprising:

a housing;

an impeller disposed within the housing and being rotatable relative to the housing to cause blood to flow through the housing;

a cannula coupled to the housing and extending distally from the housing, the cannula having a body extending between a proximal section and a distal section of the cannula positioned opposite the proximal section, the cannula configured such that the blood may flow in a proximal direction through the cannula from blood inlet to a blood outlet;

an expandable element arranged around the body of the cannula, the expandable element positioned proximal to the blood inlet, the expandable element capable of inflation and deflation; and wherein the expandable element is configured for providing an atraumatic portion of the cannula.

11. The percutaneous circulatory support device of claim 10, wherein the expandable element is positioned near the distal section of the cannula.

12. The percutaneous circulatory support device of claim 10, wherein the expandable element has an initial diameter and an inflated diameter, the expanded diameter being greater than the initial diameter.

13. The percutaneous circulatory support device of claim 10, wherein the expandable element has a circular cross section and defines a lumen extending through the expandable element.

14. A method for positioning a blood pump within a subject, the blood pump comprising a housing with an impeller disposed within the housing, a cannula extending distally from the housing, the cannula having a body extending between a proximal section and a distal section of the cannula, the cannula including one or more blood inlets positioned at the distal section, and the cannula having an expandable element positioned around the cannula body at a position that is proximal of the one or more blood inlets, the method comprising:

advancing the blood pump distally through the vasculature of the subject;

inflating the expandable element from an initial diameter to an inflated diameter; and crossing the aortic valve of the subject with the blood pump such that the distal section of the cannula is positioned at least partially in the left ventricle of the subject.

15. The method of claim 14, wherein after inflating the expandable element, the expandable element comprises a circular cross-sectional shape.

16. The method of claim 14, wherein an outer diameter of the cannula is less than the inflated diameter of the expandable element.

17. The method of claim 14, wherein the expandable element is configured for providing an atraumatic tip.

18. The method of claim 14, wherein the expandable element is a balloon.

19. The method of claim 14, wherein the expandable element comprises a lumen for receiving the body of the cannula.

* * * * *